(12) United States Patent
Decampo et al.

(10) Patent No.: US 9,469,620 B2
(45) Date of Patent: Oct. 18, 2016

(54) PROCESS FOR FORMING A PRIMARY, A SECONDARY OR A TERTIARY AMINE VIA A DIRECT AMINATION REACTION

(71) Applicants: RHODIA OPERATIONS, Paris (FR); CENTRE NATIONAL DE LA RECHERCHE SCIENTIFIQUE (C.N.R.S.), Paris (FR)

(72) Inventors: Floryan Decampo, Milan (IT); Damien Cartigny, Shanghai (CN); Mohamad Ousmane, Shanghai (CN); Marc Pera Titus, Shanghai (CN)

(73) Assignees: RHODIA OPERATIONS, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/652,493

(22) PCT Filed: Dec. 20, 2013

(86) PCT No.: PCT/CN2013/090084
§ 371 (c)(1),
(2) Date: Jun. 16, 2015

(87) PCT Pub. No.: WO2014/094650
PCT Pub. Date: Jun. 26, 2014

(65) Prior Publication Data
US 2015/0344453 A1 Dec. 3, 2015

(30) Foreign Application Priority Data
Dec. 21, 2012 (WO) .............. PCT/CN2012/087156

(51) Int. Cl.
| | | |
|---|---|---|
| *C07C 209/16* | (2006.01) | |
| *B01J 31/12* | (2006.01) | |
| *C07D 307/52* | (2006.01) | |
| *C07C 211/46* | (2006.01) | |
| *C07C 211/01* | (2006.01) | |
| *C07F 5/00* | (2006.01) | |
| *C07F 15/02* | (2006.01) | |
| *C07F 7/28* | (2006.01) | |
| *C07F 9/00* | (2006.01) | |
| *B01J 31/18* | (2006.01) | |
| *C07C 209/18* | (2006.01) | |
| *C07C 211/27* | (2006.01) | |
| *C07C 211/52* | (2006.01) | |
| *C07C 211/54* | (2006.01) | |
| *B01J 31/14* | (2006.01) | |

(52) U.S. Cl.
CPC .......... *C07D 307/52* (2013.01); *B01J 31/1805* (2013.01); *C07C 209/16* (2013.01); *C07C 209/18* (2013.01); *C07C 211/01* (2013.01); *C07C 211/27* (2013.01); *C07C 211/46* (2013.01); *C07C 211/52* (2013.01); *C07C 211/54* (2013.01); *C07F 5/003* (2013.01); *C07F 7/28* (2013.01); *C07F 9/005* (2013.01); *C07F 15/025* (2013.01); *B01J 31/12* (2013.01); *B01J 31/14* (2013.01); *B01J 2231/44* (2013.01); *B01J 2531/38* (2013.01); *B01J 2531/46* (2013.01); *B01J 2531/56* (2013.01); *B01J 2531/842* (2013.01)

(58) Field of Classification Search
CPC .... C07C 209/16; B01J 31/12; B01J 31/1805
See application file for complete search history.

(56) References Cited

U.S. PATENT DOCUMENTS

| | | | | |
|---|---|---|---|---|
| 2,918,387 A | * | 12/1959 | Wooding | ............... B05D 5/083 |
| | | | | 427/353 |
| 3,272,648 A | * | 9/1966 | Yamamoto | ............... C08K 5/19 |
| | | | | 428/422 |
| 5,266,730 A | | 11/1993 | Abe et al. | |

FOREIGN PATENT DOCUMENTS

| | | |
|---|---|---|
| CN | 1237163 A | 12/1999 |
| CN | 102146007 A | 8/2011 |

OTHER PUBLICATIONS

Hyun et al.—Mechanistic Evaluation of the Resolution of a-Amino Acids on Dynamic Chiral Stationary Phases Derived from Amino Alcohols by Ligand-Exchange Chromatography, Journal of Chromatography A, 1994, vol. 684, No. 2, pp. 189-200 (12 pages).
Aurora Fine Chemicals LLC, N-Dodecyl-4-Fluoroaniline, Jul. 3, 2013. [retrived on Mar. 18, 2014]. Retrieved from: SIN International, Accession No. 0134829156.
Antoniotti et al.—Metal Triflimidates: Better than Metal Triflates as Catalysts in Organic Synthesis—The Effect of a Highly De localized Counteranion, Angewandte Chemie International Edition, 2010, vol. 49, No. 43, pp. 7860-7888 (29 pages).
Monfardini, et al.—Mass Spectrometric Characterization of Metal Triflates and Triflimides (Lewis Superacid Catalysts) by Electrospray Ionization and Tandem Mass Spectrometry, Rapid Commun. Mass Spectrom., 2010, vol. 24, No. 17, pp. 2611-2619 (9 pages).
Brandner et al.—Luminescence Properties and Quenching Mechanisms of Ln(Tf2N)3 Complexes in the Ionic Liquid Bmpyr Tf2N, Inorganic Chemistry, 2011, vol. 50, No. 14, pp. 6509-6520 (12 pages).
Ohshima et al.—Aluminum Triflate as a Powerful Catalyst for Direct Amination of Alcohols, Including Electron-Withdrawing Group-Substituted Benzhydrols, Advanced Synthesis & Catalysis, Sep. 17, 2012, vol. 354, No. 13, pp. 2447-2452 (6 pages).
Guillena et al.—Hydrogen Autotransfer in the N-Alkylation of Amines and Related Compounds Using Alcohols and Amines as Electrophiles, Chemical Reviews, 2010, vol. 110, No. 3, pp. 1611-1641 (31 pages).

(Continued)

*Primary Examiner* — Golam M M Shameem

(57) ABSTRACT

The present invention concerns a process to obtain primary, secondary or tertiary amines, via a direct amination reaction of alcohols in presence of bis(perfluoroalkylsulfonimide) acid or salts thereof catalysts, and derivatives.

17 Claims, No Drawings

(56) References Cited

OTHER PUBLICATIONS

Haniti et al.—Borrowing Hydrogen in the Activation of Alcohols; Adv. Synth. Catal. 2006, 349, pp. 1555-1575 (21 pages).
Nixon et al.—Transition Metal Catalyzed Reactions of Alcohols Using Borrowing Hydrogen Methodology; Dalton Trans. 2009, 753 (10 pages).
Dobereiner et al.—Dehydrogenation as a Substrate-Activating Strategy in Homogenous Transition-Metal Catalysis, Chem. Rev. 2010, 110, pp. 681-703 (23 pages).
Bahn et al.—The Catalytic Amination of Alcohols; ChemCatChem 2011, 3, pp. 1853-1864 (12 pages).
Zhao et al.—Iron/Amino Acid Catalyzed Direct N-Alkylation of Amines with Alcohols; Agnew. Chem. Int. Ed. 2011, 50, pp. 3006-3009 (4 pages).

\* cited by examiner

PROCESS FOR FORMING A PRIMARY, A SECONDARY OR A TERTIARY AMINE VIA A DIRECT AMINATION REACTION

This application is a U.S. national phase entry under 35 U.S.C. §371 of International Application No. PCT/CN2013/090084, filed on Dec. 20, 2013, which claims priority to International Application No. PCT/CN2012/087156, filed on Dec. 21, 2012, the entirety of which is being incorporated herein by reference for all purposes.

The present invention concerns a process to obtain primary, secondary or tertiary amines, via a direct amination reaction of alcohols in presence of bis(perfluoroalkylsulfonimide) acid or salts thereof catalysts, and derivatives.

PRIOR ART

The following discussion of the prior art is provided to place the invention in an appropriate technical context and enable the advantages of it to be more fully understood. It should be appreciated, however, that any discussion of the prior art throughout the specification should not be considered as an express or implied admission that such prior art is widely known or forms part of common general knowledge in the field.

Amines are of significant importance for the chemical industry, but also for numerous biological processes. For instance, amino acids and nucleotides constitute essential biological building blocks and numerous bioactive compounds such as vitamins, hormones, alkaloids, neurotransmitters, or natural toxics contain amino groups. It is, therefore, not surprising, that numerous amines and their derivatives find application as agrochemicals, pharmaceuticals, or food additives. Among the several million annual tons of amines that are produced annually, higher amines are widely used in both the bulk and fine chemical industries as fundamental materials, additives, dyes, and agrochemicals.

The most common strategies to produce secondary or tertiary amines involve treating a primary amine with an alkylating reagent having a good leaving group, such as RX with X=halide, OTs or OTf. The main drawback of this conventional approach is the generation of a stoichiometric amount of wasteful (in)organic salts, as well as low secondary/tertiary amine product selectivity.

In recent years, N-monoalkylation was demonstrated, wherein an alcohol is used in place of RX and transition metal catalysis involves Ru, Ir, Cu, or Ag catalyst precursors. M. H. S. A. Hamid, P. A. Slatford, J. M. J. Williams, *Adv. Synth. Catal.* 2007, 349, 1555; T. D. Nixon, M. K. Whittlesey, J. M. J. Williams, Dalton Trans. 2009, 753; G. Guillena, D. J. Ramón, M. Yus, *Chem. Rev.* 2010, 110, 1611; G. E. Dobereiner, R. H. Crabtree, *Chem. Rev.* 2010, 110, 681. S. Bähn, S. Imm, L. Neubert, M. Zhang, H. Neumann, M. Beller, *ChemCatChem* 2011, 3, 1853. These transition metal-catalyzed N-alkylations are usually redox-type reactions involving a "borrowing hydrogen" or "hydrogen auto-transfer" mechanism (alcohol oxidation/imine formation/imine hydrogenation).

Although these reactions have found many applications using benzylic-type and saturated alcohols as the N-alkylating agents, the supposedly generated metal hydride species are incompatible with some functional groups, including olefins.

A novel straightforward method of N-alkylation using iron catalysis, such as FeBr$_3$, which involves a substitution ($S_N$) at the sp$^3$-carbon atom bearing the hydroxy group of the alcohol was also described in 2011 (Y. Zhao, S. Wan Foo, S. Saito, *Angew. Chem. Int. Ed.* 2011, 50, 3006).

Specifically, Al(OTf)$_3$ was recently used as a catalyst for direct amination of conjugated allylic alcohols and benzylic type alcohols. It appears however that this proposed catalyst leads to a non sufficient conversion of the aniline plus benzyl alcohol reaction (K. Mashima et al., Adv. Synt. Catal. 2012, 354, 2447).

It exists then a need to provide new catalysts to produce different amines by direct amination of alcohols with a sufficient yield, high conversion and an improved reaction selectivity, notably permitting then to produce amines by shifting from conventional petrochemical feedstocks towards biomass-based feedstocks.

Invention

It appears now that the use of particular bis(perfluoroalkylsulfonimide) acids or salts thereof as catalysts in presence of alcohols and amines permits to produce primary, secondary or tertiary amines with a high yield, selectivity and conversion as well. Moreover, these catalysts belonging to a new generation of environmentally-friendly catalysts can shorten the reaction time and are efficient with a catalyst loading that remains relatively low. The reaction of the present invention is also attractive from an environmental plan as water is the sole by-product.

The present invention concerns then a process for forming a primary, a secondary or a tertiary amine, via a direct amination reaction, comprising at least reacting:
1) a first reactant being a compound having at least one primary, secondary or tertiary hydroxyl function, with
2) a second reactant being NH$_3$ or a compound having at least one primary or secondary amine function,
at least in the presence of a catalyst of formula (I):

$$M[RF\text{—}SO_2\text{—}N\text{—}SO_2\text{—}R'F]_n \quad (I)$$

wherein:
RF and R'F, which are identical or different, each represent a perhalogen radical; and
M is H or an element chosen from: transition metal, post transition metal, poor metal elements in the p-block and lanthanide,
n is an integer equal to the valence of M.

The present invention also concerns primary, secondary or tertiary amines susceptible to be obtained according to the process of the invention.

The present invention also concerns 3 new compounds notably obtained by the process as follows: N-(1-phenylethyl)dodecan-1-amine (C$_{20}$H$_{35}$N/M$_w$=289.50 g/mol), N-dodecyl-4-fluoroaniline (C$_{18}$H$_{30}$FN/M$_w$=279.44 g/mol) and N,4-dibenzylaniline (C$_{20}$H$_{19}$N/M$_w$=273.37 g/mol).

The present invention also concerns new compounds, that may notably be used as catalysts for the process of the invention, chosen in the groups consisting of: Ce(NTf$_2$)$_3$, Fe(NTf$_2$)$_3$, Ti(NTf$_2$)$_4$, Pr(NTf$_2$)$_3$ and V(NTf$_2$)$_4$.

DETAILS OF THE INVENTION

Throughout the description, including the claims, the term "comprising one" should be understood as being synonymous with the term "comprising at least one", unless otherwise specified, and "between" should be understood as being inclusive of the limits.

"Alkyl" as used herein means a straight chain or branched saturated aliphatic hydrocarbon. Preferably alkyl group comprises 1-18 carbon atoms. Representative saturated straight chain alkyls include methyl, ethyl, n-propyl, n-butyl, n-pentyl, and the like; while saturated branched alkyls include isopropyl, sec-butyl, isobutyl, tert-butyl, isopentyl, and the like.

"Alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbon atoms of the alkenyl group. Representative unsaturated straight chain alkenyls include ethenyl, propenyl, butenyl, pentenyl, hexenyl, heptenyl, octenyl, nonenyl, decenyl and the like.

The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups.

"Aryl" as used herein means a 6-carbons monocyclic or 10-carbons bicyclic aromatic ring system wherein 0, 1, 2, 3, or 4 atoms of each ring are substituted. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

"Cycloalkyl" as used herein means cycloalkyl groups containing from 3 to 8 carbon atoms, such as for example cyclohexyl.

"Heterocyclic" as used herein means heterocyclic groups containing up to 6 carbon atoms together with 1 or 2 heteroatoms which are usually selected from O, N and S, such as for example radicals of: oxirane, oxirene, oxetane, oxete, oxetium, oxalane (tetrahydrofurane), oxole, furane, oxane, pyrane, dioxin, dioxane, pyranium, oxepane, oxepine, oxocane, oxocinc groups, aziridine, azirine, azirene, azetidine, azetine, azete, azolidine, azoline, azole, azinane, tetrahydropyridine, tetrahydrotetrazine, dihydroazine, azine, azepane, azepine, azocane, dihydroazocine, azocinic groups and thiirane, thiirene, thiethane, thiirene, thietane, thiete, thietium, thiolane, thiole, thiophene, thiane, thiopyrane, thiine, thiinium, thiepane, thiepine, thiocane, thiocinic groups.

"Heterocyclic" may also mean a heterocyclic group fused with a benzene-ring wherein the fused rings contain carbon atoms together with 1 or 2 heteroatom's which are selected from N, O and S.

The first reactant of the invention is a compound having at least one primary, secondary or tertiary hydroxyl function. This compound can notably be a compound comprising two, similar or different, primary, secondary or tertiary hydroxyl functions. Preferably, the first reactant is a compound comprising one or two primary hydroxyl function.

This first reactant may notably be a compound of formula (II):

Wherein:
x is 1 or 2
$R^1$ is H or a straight, branched and/or cyclic hydrocarbon group
$R^1$ may represent straight, branched/and/or cyclic hydrocarbon group that can be an alkyl, alkenyl, aryl, cycloalkyl or heterocyclic group, eventually comprising one or several heteroatoms such as O, S, F, and N. Preferred groups for $R^1$ may be for example: H, alkyl, cyclic alkane, cyclic alkene, phenyl, furanyl, and tetrahydrofuranyl.

In addition the first reactant may comprise additional functionalities. The additional functionalities may behave as electron donating or electron withdrawing groups. There is no particular limitation on the number of carbon atoms present in the reactant as long as its structure does not prevent the direct amination reaction.

According to a preferred embodiment of the present invention, the first reactant does not comprise a simple or double insaturation connected to the β-carbon carrying the hydroxyl function, as in the case of allylic alcohols or propargylic alcohols.

Preferred first reactants of the present invention, such as compounds of formula (II), are chosen in the group consisting of: furfuryl alcohol, 2,5 furandimethanol, 2,5-tetrahydrofuranedimethanol, benzyl alcohol, α-methylbenzyl alcohol, 1,6-hexanediol, 1,2-cyclohexanediol, 1,4-cyclohexanediol, 1-phenylethanol, 1,7-heptandiol, lauryl alcohol and isosorbide.

It has to be noticed that it's perfectly possible to use several first reactant types during the reaction of the present invention.

Concentration of the first reactant may be comprised between 0.001 and 10 mol·L$^{-1}$, when a solvent is used in the reaction medium.

The second reactant of the invention is $NH_3$ or a compound having at least one primary or secondary amine function.

This second reactant may notably be a compound of formula (III):

Wherein:
$R^2$ is H or a straight, branched and/or cyclic hydrocarbon group
$R^2$ may represent straight, branched and/or cyclic hydrocarbon group that can be an alkyl, alkenyl, aryl, cycloalkyl or heterocyclic group, eventually comprising one or several heteroatoms such as O, S, F, and N. Preferred groups for $R^2$ may be for example: H, alkyl, phenyl, benzyl, cycloalkyl, and cycloalkene.

This second reactant may also be a compound of formula (V):

Wherein:
$R^3$ and $R^4$ represent, independently from each other, a straight, branched and/or cyclic hydrocarbon group, $R^3$ and $R^4$ may together form a cyclic group, which may optionally contain a heteroatom. Said cyclic group may notably be an alicyclic group and/or an aromatic group.
$R^3$ and/or $R^4$ may represent straight, branched and/or cyclic hydrocarbon group that can be an alkyl, alkenyl, aryl, cycloalkyl or heterocyclic group, eventually comprising one or several heteroatoms such as O, S, F, and N. Preferred groups for $R^3$ and $R^4$ may be for example: alkyl, phenyl, benzyl, cycloalkyl, and cycloalkene. R4 may then form together a cyclic group such as a heterocyclic amine. Cyclic groups formed by $R^3$ and $R^4$ may comprise from 2 to 20 carbon atoms and optionally a heteroatom such as O, S, F, and N.

In addition, the second reactant may comprise additional functionalities. The additional functionalities may behave as electron donating or electron withdrawing groups. There is no particular limitation on the number of carbon atoms present in the reactant as long as its structure does not prevent the direct amination reaction.

Preferred second reactants of the present invention, such as compounds of formula (III), are chosen in the group consisting of: ammonia, phenylamine, n-heptylamine, aniline, 4-fluoro aniline, 4-benzyl aniline, methylamine, and dodecylamine.

Preferred second reactants of the present invention, such as compounds of formula (V), are chosen in the group consisting of: pyrrolidine, pyrrol, pyridine, imidazole, quinoleine tetrahydroquinoleine, aziridine, azirine, dimethylamine and piperidine.

It has to be noticed that it's perfectly possible to use several second reactant types during the reaction of the present invention.

Concentration of the second reactant may be comprised between 0.001 and 10 mol·L$^{-1}$, when a solvent is used in the reaction medium.

According to a particular embodiment of the present invention, the reaction medium can comprise, notably at the start of the reaction, between 0.1 and 5 molar equivalent of the second reactant for 1 molar equivalent of the first reactant, notably between 1 and 3 molar equivalent of the second reactant for 1 molar equivalent of the first reactant in order to selectively produce secondary amine products in the reaction, notably between 0.1 and 0.5 molar equivalent of the second reactant for 1 molar equivalent of the first reactant in order to selectively produce tertiary amine products.

The amine obtained according to the process of the present invention may be a primary, a secondary or a tertiary amine, preferably a primary or a secondary amine.

The primary or secondary amine of the present invention may notably be a compound of formula (IV):

$$R^1(CH_2-NHR^2)_x \quad (IV)$$

Wherein:
x is 1 or 2
$R^1$ is H or a straight, branched and/or cyclic hydrocarbon group
$R^2$ is H or a straight, branched and/or cyclic hydrocarbon group Preferred primary or second amines of the invention, such as compounds of formula (IV), are chosen in the group consisting of: N-phenylbenzylamine (N-benzylaniline), dibenzylamine, N-(1-phenylethyl)aniline, 1-benzyl-1,2,3,4-tetrahydroquinoline, N-(cyclohex-2-en-1-yl)benzenamine, (tetrahydrofuran-2,5-diyl)dimethanamine, (furan-2,5-diyl)dimethanamine, 1,6-hexamethylenediamine, 1,1'-(tetrahydrofuran-2,5-diyl)bis(N-methylmethylamine), 1,1'-(tetrahydrofuran-2,5-diyl)bis(N-heptaneaminomethane), N-(1-phenylethyl) dodecan-1-amine, N-dodecyl-4-fluoroaniline, N,4-dibenzylaniline and N-(furan-2-ylmethyl) aniline.

Reaction of the present invention may notably be represented as follows:

$$xH_2O$$

More preferably, reaction of the present invention can be represented as follows:

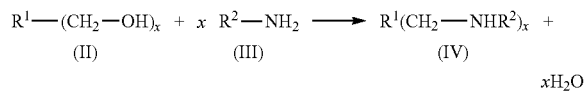

Preferred reactions according to the process of the present invention are the following:
reaction of benzylalcohol and aniline to produce N-phenyl benzylamine (N-benzylaniline)
reaction of 2,5-tetrahydrofurandimethanol and ammonia to produce (tetrahydrofuran-2,5-diyl)dimethanamine
reaction of 2,5-furandimethanol with ammonia to produce (furan-2,5-diyl)dimethanamine
reaction of 1,6-hexandiol with ammonia to produce 1,6-hexamethylenediamine
reaction of 2,5-tetrahydrofuranedimethanol with N-heptylamine to produce 1,1'-(tetrahydrofuran-2,5-diyl)bis(N-heptaneaminomethane)

Concerning the catalyst of formula (I), RF and R'F, which are identical or different, represent a perhalogen radical, which is preferably having from 1 to 12 carbon atoms. Halogen atoms in the perhalogen radicals may be for example F or Cl. Preferably RF and R'F, which are identical or different, represent $CF_3$.

Elements of the periodic table may be chosen in the group consisting of:
transition metals, also known as elements of d block, such as preferably Ti, Y, Zn, V, Cu or Fe.
post-transition metals, usually composed of Ga, In, Tl, Sn, Pb, Bi and Po, such as preferably Bi,
poor metal elements in the p-block, such as Al, and
lanthanides, such as La, Ce, Pr, Eu, Yb and Nd.

Poor metal elements in the p-block of the periodic table describe a metallic element selected from aluminium, gallium, indium, thallium, tin, lead, bismuth and polonium.

Catalysts of the present invention are preferably chosen in the group consisting of: $H(NTf_2)$, $Ce(NTf_2)_3$, $Fe(NTf_2)_3$, $Y(NTf_2)_3$, $La(NTf_2)_3$, $Bi(NTf_2)_3$, $Al(NTf_2)_3$, $Ti(NTf_2)_4$, $Pr(NTf_2)_3$, $Eu(NTf_2)_3$, $Yb(NTf_2)_3$, and $V(NTf_2)_4$.

The present invention also concerns new compounds chosen in the groups consisting of: $Ce(NTf_2)_3$, $Fe(NTf_2)_3$, $Ti(NTf_2)_4$, $Pr(NTf_2)_3$ and $V(NTf_2)_4$.

These compounds may notably be produced by reaction of metal, hydroxide metal and/or oxide metal with bistrifluoromethanesulfonimide (TFSIH), usually at a temperature comprised between 10 and 150° C.

A combination of two or more catalysts may be used during the reaction of the present invention, notably in blend.

Catalyst loading during the reaction may be comprised between 0.01 and 50 mol %, preferably between 0.1 and 30 mol %, more preferably between 1 and 10 mol %, in relation with the molar amount of the reactant in default.

Catalyst of the invention may be used in a homogeneous or heterogeneous way.

Catalyst may be supported on a carrier, such as for example one of the oxides, carbons or organic or inorganic resins. Notably, the carrier may be selected from the group consisting of silica, alumina, zirconia, titania, ceria, magnesia, lanthania, niobia, yttria, zeolite, perovskite, silica clay, and iron oxide and mixtures thereof. The catalyst may be supported on a carrier in any convenient fashion, particularly by adsorption, ion-exchange, grafting, trapping, impregnation, or sublimation.

Reaction of the present invention may be carried out by using a catalyst-ligand complex in which catalyst is the compound of formula (I). Although there are no particular restrictions on the ligand in the present invention provided it is a Lewis base having the ability to coordinate to a catalyst of formula (I), ligand is preferably chosen in the family of carbene ligand, π-type ligand, phosphorous ligand, oxygen ligand and nitrogen ligand. Suitable ligands to be used according to the present invention are phosphorus ligands such as halophosphites, for example fluorophosphites, phosphites, phosphinites, phosphonites, and phosphine. Monodentate phosphine ligands and bidentate diphosphine ligands, such as xantphos, are particularly preferred. Other suitable ligands to be used according to the present invention are pyridine based ligands such as bipyridine and terpyridine.

It has to be noticed that the catalyst-ligand complex may be prepared before the start of the reaction of the present invention or in situ at the start or during the reaction.

The process of the present invention may be carried out without solvent. It is also possible to use a solvent or a combination of solvents for the reaction, preferably solvents able to dissolve the first reactant and the second reactant.

Preferred solvents to be used in the process of the invention are apolar solvents, polar aprotic solvents or water.

Apolar solvents are preferably chosen in the group constituting of: hexane, cyclohexane, pentane, cyclopentane, benzene, trimethyl benzene, toluene, xylene, diethyl ether, and chloroform.

Polar aprotic solvents, are preferably chosen in the group constituting of:
- linear ethers, such as diethylether, dimethoxyethane (glyme) or bis(2-methoxyethyl) ether (diglyme) or cyclic ethers, such as tetrahydrofuran, dioxane, methyltetrahydrofuran or dimethyltetrahydrofuran,
- esters, such as methyl or ethyl formate, propylene or ethylene carbonate, or butyrolactones,
- nitriles, acetonitriles, benzonitriles,
- nitrate derivatives, such as nitromethane or nitrobenzene,
- amides, such as dimethylformamide, diethylformamide and N-methylpyrolidone,
- sulfones, such as dimethyl sulfone, tetramethylene sulfone and other sulfolanes.
- sulfoxides, such as DMSO.

A combination of two or more solvents in blend may be used during the reaction of the present invention.

The temperature at which reaction is performed may vary in a large range, but in general it is preferred that the reaction is carried out at a temperature from 0 and 300° C., more preferably between 50 and 200° C., notably between 120 and 180° C. Temperatures may be reached either thermally or by microwave irradiation.

Pressure range of the reaction may be comprised between 1 and 100 bar. Reaction of the present invention may be carried out for a range time comprised between 10 min to 24 hours, preferably between 1 hour and 8 hours.

The reaction may be carried out in the presence of air or an inert atmosphere such as $N_2$, Ar, $CO_2$ or even $NH_3$. Suitable oxygen containing gases include air, oxygen gas, and mixtures of oxygen gas with other gases such as nitrogen or argon. In some embodiments the oxygen containing gas is a flowing oxygen containing gas. In other embodiments the reaction vessel is charged with the oxygen containing gas.

This reaction may be conducted in any conventional equipment suitable to effect production of amines. This reaction may be carried out in a continuous or a discontinuous fashion. For example, suitable equipments include a stirred tank or loop reactor.

End of reaction may be carried out by stop of the temperature and cooling of the reaction medium, notably air cooling.

The efficiency of the process of the present invention can be monitored by any conventional analytical means, such as Infrared spectroscopy, NMR, Raman spectroscopy, GC, HPLC and SFC.

At the end of the reaction, catalysts may be eventually neutralized and/or removed by distillation, extraction or washings. Said catalysts may notably be recycled to the reactor.

Amines of interest can be purified by well known methods of the technical field, such as distillation, crystallization, liquid extraction or extraction with a polymer to adsorb amines.

The examples provided here further describe and demonstrate embodiments of the present invention. The examples are given solely for the purpose of illustration and are not to be construed as limitation of the present invention.

EXPERIMENTAL PART

Example 1

5 mol % of different catalysts are blended with a solution comprising 2 molar equivalents of aniline for 1 molar equivalent of benzyl alcohol and toluene as solvent (concentration of benzyl alcohol in solvent is 2 mol·L$^{-1}$). Reaction occurs under microwave irradiation at a temperature of 160° C. for 2 hours to produce N-benzylaniline.

Results determined by $^1$H NMR analysis are mentioned in Table 1:

TABLE 1

| No | Catalyst | Conversion of benzyl alcohol in N-benzylaniline (%) |
|---|---|---|
| C1 | — | <1 |
| C2 | Cs(OTf) | <1 |
| C3 | Cu(OTf)$_2$ | <1 |
| C4 | Al(OTf)$_3$ | 17 |
| C5 | K(NTf) | <1 |
| C6 | Cu(NTf)$_2$ | <1 |
| C7 | Ca(NTf$_2$)$_2$ | <1 |
| C8 | FeBr$_3$ | 8 |
| 1 | Ce(NTf$_2$)$_3$ | 29 |
| 2 | Fe(NTf$_2$)$_3$ | 32 |
| 3 | Y(NTf$_2$)$_3$ | 37 |
| 4 | La(NTf$_2$)$_3$ | 46 |
| 5 | Bi(NTf$_2$)$_3$ | 51 |
| 6 | Al(NTf$_2$)$_3$ | 52 |
| 7 | Ti(NTf$_2$)$_4$ | 78 |
| 8 | Pr(NTf$_2$)$_3$ | 80 |
| 9 | Eu(NTf$_2$)$_3$ | 87 |
| 10 | Yb(NTf$_2$)$_3$ | 88 |
| 11 | V(NTf$_2$)$_4$ | 94 |

No imine formation nor tertiary amine was detected at the end of the reaction with trials 1-7, by $^1$H NMR analysis.

It appears then that use of the catalyst of the present invention permits to produce amines via direct amination with a sufficient conversion, notably in comparison with the FeBr$_3$ and Al(OTf)$_3$ catalysts mentioned in the prior art.

Example 2

5 mol % of different catalysts are blended with the solution presented in Example 1 and 5 mol % of xantphos ligand [4,5-Bis(diphenylphosphino)-9,9-dimethylxanthene]. Reaction occurs under microwave irradiation at a temperature of 160° C. for 2 hours.

Results determined by $^1$H NMR analysis are mentioned in Table 2:

TABLE 2

| No | Catalyst | Ligand (mol %) | Conversion of benzyl alcohol in N-benzylaniline (%) |
|---|---|---|---|
| C1 | — | — | <1 |
| 1 | Al(NTf$_2$)$_3$ | Xantphos (5) | 59 |
| 2 | Bi(NTf$_2$)$_3$ | Xantphos (5) | 61 |
| 3 | Bi(NTf$_2$)$_3$ | PPh3 (10) | 61 |
| 4 | Ti(NTf$_2$)$_4$ | PPh3 (10) | 85 |
| 5 | Ti(NTf$_2$)$_4$ | Xantphos (5) | 95 |

No imine formation nor tertiary amine was detected at the end of the reaction with trials 1-5, by $^1$H NMR analysis.

It appears then that a diphosphine ligand such as Xantphos is efficiently activating catalysts of the present invention that permits to provide a higher conversion to the reaction.

Example 3

5 mol % of catalysts are blended with a solution comprising 1 molar equivalents of amine for 1 molar equivalent of alcohol and toluene as solvent (concentration of alcohol in solvent is 2 mol·L$^{-1}$) and 10 mol % of ligand. Reaction occurs under microwave irradiation at specified temperature and time.

Results determined by $^1$H NMR analysis are mentioned in Table 3:

TABLE 3

| Catalyst/ Ligand | Amine Alcohol | Temperature Time | Product | Conversion (%) |
|---|---|---|---|---|
| V(NTf$_2$)$_4$/ Bipyridine | heptan-1-amine/α-methylbenzyl alcohol | 200° C./16 h | N-(1-phenylethyl)dodecan-1-amine | 100 |
| V(NTf$_2$)$_4$/ Bipyridine | 4-fluro aniline/ lauryl alcohol | 200° C./16 h | N-dodecyl-4-fluoroaniline | 58 |
| Ti(NTf$_2$)$_4$ Terpyridine | 4-benzyl aniline/ benzyl alcohol | 160° C./1 h | N,4-dibenzylaniline | 66 |
| Ti(NTf$_2$)$_4$ Terpyridine | aniline/ furfuryl alcohol | 160° C./1 h | N-(furan-2-ylmethyl) aniline | 98 |

No imine formation nor tertiary amine was detected at the end of the reaction with trials 1-7, by $^1$H NMR analysis.

N-(1-phenylethyl)dodecan-1-amine: C$_{20}$H$_{35}$N/ M$_w$=289.50 g/mol $^1$H NMR (300 MHz, CDCl$_3$) δ 7.32-7.25 (m, 5H), 3.75 (q, J=6.6 Hz, 1H), 2.63 (m, 2H), 1.59-1.56 (m, 2H), 1.48-1.21 (m, 22H), 0.88 (t, J=6.6 Hz, 3H).

$^{13}$C NMR (75 MHz, CDCl$_3$) δ 145.9, 128.3, 126.7, 126.4, 58.3, 47.8, 31.8, 30.2, 27.0, 29.6, 29.5, 29.4, 29.2, 27.3, 24.3, 22.6, 22.0, 14.1.

N-dodecyl-4-fluoroaniline: C$_{18}$H$_{30}$FN/M$_w$=279.44 g/mol $^1$H NMR (300 MHz, CDCl$_3$) δ 6.89 (m, 2H), 6.58-6.52 (m, 2H), 3.53 (br, 1H), 3.07 (t, J=6.9 Hz, 2H), 1.57 (m, 2H), 1.48-1.21 (m, 18H), 0.88 (t, J=6.6 Hz, 3H).

$^{13}$C NMR (75 MHz, CDCl$_3$) δ 155.6 (d, J$_{CF}$=234.4 Hz), 144.9, 115.5 (d, J$_{CF}$=22.3 Hz), 113.4 (d, J$_{CF}$=7.3 Hz), 44.7, 31.8, 31.6, 30.4, 29.8, 29.7, 29.6, 29.5, 27.1, 26.8, 22.6, 14.1.

N,4-dibenzylaniline: C$_{20}$H$_{19}$N/M$_w$=273.37 g/mol $^1$H NMR (300 MHz, CDCl$_3$) δ 7.44-7.21 (m, 10H), 7.08-7.05 (d, J=8.4 Hz, 2H), 6.65-6.62 (d, 2H), 4.35 (s, 2H), 4.12 (br, 1H), 3.94 (s, 2H).

$^{13}$C NMR (75 MHz, CDCl$_3$) δ 146.6, 142.2, 139.7, 130.8, 129.9, 129.0, 128.8, 128.6, 127.7, 127.4, 126.9, 113.2, 48.6, 41.3.

Example 4

Synthesis of Ti(NTf$_2$)$_4$

Titanium powder (4.8 g, 0.1 mol) was added to a 200 ml aqueous solution of TFSIH (86%, 160 g, 0.5 mol) and the mixture was allowed to stir for 2 days at reflux (105° C.). This crude material was then cooled to room temperature and filtrated. This filtrate was further purified by distillation under reduced pressure. After a final drying under reduced pressure while heating at 100° C., 60 g of the desired product was afforded as a pink solid.

$^{19}$F NMR (280 MHz, D$_2$O) δ -78.7.

Synthesis of Pr(NTf$_2$)$_3$

Pr$_6$O$_{11}$ (2.5 g, 0.0025 mol) was added to a 25 ml aqueous solution of TFSIH (15 g, 0.045 mol) and the mixture was allowed to stir at 60° C. for 24 h. This crude material was then cooled to room temperature and filtrated. After a final drying of this filtrate under reduced pressure, 13 g of the desired product was afforded as a green solid (88% yield).

$^{19}$F NMR (280 MHz, D$_2$O) δ -79.2.

Synthesis of V(NTf$_2$)$_4$

V$_2$O$_4$ (2.5 g, 0.015 mol) was added to a 80 ml aqueous solution of TFSIH (40 g, 0.12 mol) and the mixture was allowed to stir at 60° C. for 24 h. This crude material was then cooled to room temperature and filtrated. After a final drying of the filtrate under reduced pressure, the desired product was afforded as a blue solid.

$^{19}$F NMR (280 MHz, D$_2$O) δ -79.2.

Synthesis of Ce(NTf$_2$)$_3$

Ce$_2$(CO$_3$)$_3$ (33 g) was added to a 200 ml aqueous solution of TFSIH (100 g) and the mixture was allowed to stir at 85° C. for 24 h. This crude material was then cooled to room temperature and filtrated. After a final drying of the filtrate under reduced pressure while heating at 80° C., 88 g of the desired product was afforded as a white solid.

$^{19}$F NMR (280 MHz, D$_2$O) δ -79.3.

Synthesis of Fe(NTf$_2$)$_3$

Fe(OH)$_3$ (48.00 g, 0.45 mol) was added to a 300 ml aqueous solution of TFSIH (450 g, 1.35 mol) and the mixture was allowed to stir at 90° C. for 24 h. This crude material was then cooled to room temperature and filtrated. After a final drying of the filtrate under reduced pressure while heating at 80° C., 138 g of the desired product was afforded as a yellow solid.

$^{19}$F NMR (280 MHz, D$_2$O) δ -79.5.

What is claimed is:

1. A process for forming a primary, a secondary or a tertiary amine, via a direct amination reaction, comprising at least reacting:
   1) a first reactant being a compound having at least one primary, secondary or tertiary hydroxyl function, with 2) a second reactant being $NH_3$ or a compound having at least one primary or secondary amine function,
in the presence of a catalyst of formula (I):

$$M[RF—SO_2—N—SO_2—R'F]n \qquad (I)$$

wherein:
RF and R'F, which are identical or different, each represent a perhalogen radical; and
M is H or an element selected from the group consisting of: transition metals, post transition metals, metallic poor metal elements in the p-block and lanthanides,
n is an integer equal to the valence of M.

2. The process according to claim 1, wherein the first reactant is a compound of formula (II):

$$R^1—(CH_2OH)_x \qquad (II)$$

Wherein:
x is 1 or 2, and
$R^1$ is H or a straight, branched and/or cyclic hydrocarbon group.

3. The process according to claim 1, wherein the first reactant does not comprise a simple or double insaturation connected to the β-carbon carrying the hydroxyl function.

4. The process according to claim 1 wherein the first reactant is selected from the group consisting of: furfuryl alcohol, 2,5 furandimethanol, 2,5-tetrahydrofuranedimethanol, benzyl alcohol, α-methylbenzyl alcohol, 1,6-hexanediol, 1,2-cyclohexanediol, 1,4-cyclohexanediol, 1-phenylethanol, 1,7-heptandiol, lauryl alcohol and isosorbide.

5. The process according to claim 1, wherein the second reactant is a compound of formula (III):

$$R^2—NH_2 \qquad (III)$$

Wherein:
$R^2$ is H or a straight, branched and/or cyclic hydrocarbon group.

6. The process according to claim 1 wherein the second reactant is a compound of formula (V):

$$R^3—NH—R^4 \qquad (V)$$

Wherein:
$R^3$ and $R^4$ represent, independently from each other, a straight, branched and/or cyclic hydrocarbon group, $R^3$ and $R^4$ may together form a cyclic group, which may optionally contain a heteroatom.

7. The process according to claim 1, wherein the second reactant is selected from the group consisting of: ammonia, phenylamine, n-heptylamine, aniline, 4-fluoro aniline, 4-benzyl aniline, methylamine, and dodecylamine.

8. The process according to claim 1, wherein the second reactant is selected from the group consisting of: pyrrolidine, pyrrol, pyridine, imidazole, quinoleine tetrahydroquinoleine, aziridine, azirine, dimethylamine and piperidine.

9. The process according to claim 1, wherein the reaction medium comprises between 0.1 and 5 molar equivalent of the second reactant for 1 molar equivalent of the first reactant.

10. The process according to claim 1 wherein the primary or secondary formed amine is a compound of formula (IV):

$$R^1(CH_2—NHR^2)_x \qquad (IV)$$

Wherein:
x is 1 or 2
$R^1$ is H or a straight, branched and/or cyclic hydrocarbon group
$R^2$ is H or a straight, branched and/or cyclic hydrocarbon group.

11. The process according to claim 1, wherein the formed amine is a compound selected from the group consisting of: N-phenylbenzylamine (N-benzylaniline), dibenzylamine, N-(1-phenylethyl)aniline, 1-benzyl-1,2,3,4-tetrahydroquinoline, N-(cyclohex-2-en-1-yl)benzenamine, (tetrahydrofuran-2,5-diyl) dimethanamine, (furan-2,5-diyl) dimethanamine, 1,6-hexamethylenediamine, 1,1'-(tetrahydrofuran-2,5-diyl)bis(N-methylmethylamine), 1,1'-(tetrahydrofuran-2,5-diyl)bis(N-heptaneaminomethane), N-(1-phenylethyl)dodecan-1-amine, N-dodecyl-4-fluoroaniline, N,4-dibenzylaniline and N-(furan-2-ylmethyl) aniline.

12. The process according to claim 1, wherein M of the catalyst of formula (I) is an element selected from the group consisting of:
Ti, Y, Zn, V, Cu, Fe,
Ga, In, Tl, Sn, Pb, Bi, Po,
Al,
La, Ce, Pr, Eu, Yb and Nd.

13. The process according to claim 1, wherein the catalyst is selected from the group consisting of: $H(NTf_2)$, $Ce(NTf_2)_3$, $Fe(NTf_2)_3$, $Y(NTf_2)_3$, $La(NTf_2)_3$, $Bi(NTf_2)_3$, $Al(NTf_2)_3$, $Ti(NTf_2)_4$, $Pr(NTf_2)_3$, $Eu(NTf_2)_3$, $Yb(NTf_2)_3$, and $V(NTf_2)_4$.

14. The process according to claim 1, wherein the catalyst loading is comprised between 0.01 and 50 mol %, in relation with the molar amount of the reactant in default.

15. The process according to claim 1, wherein the catalyst is a catalyst-ligand complex.

16. The process according to claim 1, wherein a solvent is used in the reaction medium.

17. The process according to claim 16, wherein the solvent is an apolar solvent, a polar aprotic solvent or water.

* * * * *